US009827177B2

(12) United States Patent
Yuan et al.

(10) Patent No.: US 9,827,177 B2
(45) Date of Patent: *Nov. 28, 2017

(54) ANTIPERSPIRANT PRODUCTS WITH PROTEIN AND ANTIPERSPIRANT SALTS

(71) Applicant: Colgate-Palmolive Company, Piscataway, NJ (US)

(72) Inventors: Shaotang Yuan, East Brunswick, NJ (US); Long Pan, Cherry Hill, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/649,946

(22) PCT Filed: Dec. 19, 2012

(86) PCT No.: PCT/US2012/070501
§ 371 (c)(1),
(2) Date: Jun. 5, 2015

(87) PCT Pub. No.: WO2014/098819
PCT Pub. Date: Jun. 26, 2014

(65) Prior Publication Data
US 2015/0313821 A1 Nov. 5, 2015

(51) Int. Cl.
A61K 8/44 (2006.01)
A61K 8/27 (2006.01)
A61K 8/64 (2006.01)
A61Q 15/00 (2006.01)

(52) U.S. Cl.
CPC .............. A61K 8/27 (2013.01); A61K 8/44 (2013.01); A61K 8/64 (2013.01); A61Q 15/00 (2013.01); A61K 2800/58 (2013.01); A61K 2800/874 (2013.01)

(58) Field of Classification Search
CPC ... A61K 8/44; A61K 8/27; A61K 8/64; A61K 2800/58; A61K 2800/874; A61Q 15/00
See application file for complete search history.

(56) References Cited

U.S. PATENT DOCUMENTS

| 2,503,280 | A |  | 4/1950 | Lockwood |
| 2,507,088 | A |  | 5/1950 | Bradley |
| 2,527,686 | A |  | 10/1950 | Sandberg |
| 2,893,918 | A |  | 7/1959 | Abramson |
| 3,260,744 | A |  | 7/1966 | Kenkichi |
| 3,320,174 | A |  | 5/1967 | Rubinfeld |
| 3,372,188 | A |  | 3/1968 | Terence |
| 3,535,421 | A |  | 10/1970 | Briner |
| 3,538,230 | A |  | 11/1970 | Morton |
| 3,678,154 | A |  | 7/1972 | Briner |
| 3,741,911 | A |  | 6/1973 | Shane |
| 3,862,307 | A |  | 1/1975 | Giulio |
| 3,937,807 | A |  | 2/1976 | Haefele |
| 3,941,818 | A |  | 3/1976 | Abdel-Monem |
| 3,959,458 | A |  | 5/1976 | Agricola et al. |
| 4,051,234 | A |  | 9/1977 | Gieske et al. |
| 4,316,824 | A |  | 2/1982 | Pancheri |
| 4,339,432 | A |  | 7/1982 | Ritchey et al. |
| 4,340,583 | A |  | 7/1982 | Wason |
| 4,487,757 | A |  | 12/1984 | Kiozpeoplou |
| 4,565,693 | A |  | 1/1986 | Marschner |
| 4,599,152 | A |  | 7/1986 | Ashmead |
| 4,684,528 | A |  | 8/1987 | Godfrey |
| 4,687,663 | A |  | 8/1987 | Schaeffer |
| 4,842,847 | A |  | 6/1989 | Amjad |
| 4,866,161 | A |  | 9/1989 | Sikes et al. |
| 4,885,155 | A |  | 12/1989 | Parran, Jr. et al. |
| 5,004,597 | A |  | 4/1991 | Majeti et al. |
| 5,061,815 | A | * | 10/1991 | Leu ........................ A23L 1/3045 426/74 |
| 5,156,845 | A |  | 10/1992 | Grodberg |
| 5,188,821 | A |  | 2/1993 | Gaffar et al. |
| 5,192,531 | A |  | 3/1993 | Gaffar et al. |
| 5,194,262 | A | * | 3/1993 | Goldberg ................. A61K 8/11 424/401 |
| 5,504,055 | A |  | 4/1996 | Hsu |
| 5,643,559 | A |  | 7/1997 | Eigen et al. |
| 5,696,169 | A | * | 12/1997 | Otsu ....................... A61K 33/30 424/641 |
| 5,698,724 | A |  | 12/1997 | Anderson et al. |
| 5,707,679 | A |  | 1/1998 | Nelson |
| 5,714,447 | A | * | 2/1998 | Jones ....................... A61K 8/27 510/130 |
| 5,911,978 | A |  | 6/1999 | Carr et al. |

(Continued)

FOREIGN PATENT DOCUMENTS

| CN | 101606639 | 12/2009 |
| CN | 102811698 | 12/2012 |

(Continued)

OTHER PUBLICATIONS

Baumy et al (1988). "Effect of pH and ionic strength on the binding of bivalent cations to β-casein." Le Lait, 68(4): 409-418.*
Anonymous, "Zinc Lauryl Ether Sulphate, A New Approach to Skincare," , Apr. 2004, Retrieved from Internet, http://www.erwebhosting.it/zsi/repository/Zinc%20Lauryl%20Ether%20Sulphate,%20A%20new%20approach%20to%20skin%20care.pdf, Retrieved Sep. 26, 2013.
Deschaume et al., "Interactions of aluminum hydrolytic species with biomolecules," New Journal of Chemistry, 2008, 32:1346-1353.
European Food Safety Authority, "Scientific Opinion on the safety and efficacy of tetra-basic zinc chloride for all animal species," EFSA Journal, 2012, 10(5):2672.
Hartwell et al., "Preparation and characterization of tyrosine and lysine metal chelate polyesters and polyamides", J. of the American Chem. Society, Mar. 1970, 92(5):1284-1289.
International Search Report and Written Opinion for International Application No. PCT/US2012/070489 dated Oct. 22, 2013.

(Continued)

Primary Examiner — Anoop Singh
Assistant Examiner — Doan Phan

(57) ABSTRACT

The invention provides antiperspirant formulations comprising a protein and an antiperspirant salt in combination with a cosmetically acceptable carrier, together with methods of making and using these complexes and compositions.

15 Claims, No Drawings

(56) References Cited

U.S. PATENT DOCUMENTS

| | | | |
|---|---|---|---|
| 5,993,784 A | 11/1999 | Hill | |
| 6,121,315 A | 9/2000 | Nair et al. | |
| 6,156,293 A | 12/2000 | Jutila et al. | |
| 6,607,711 B2 | 8/2003 | Pedersen | |
| 6,685,920 B2 | 2/2004 | Baig et al. | |
| 6,969,510 B2 | 11/2005 | Holerca et al. | |
| 8,067,627 B2 | 11/2011 | Newsome et al. | |
| 8,247,398 B2 | 8/2012 | Goel | |
| 2003/0059385 A1* | 3/2003 | Ansmann | A61K 8/0241 424/66 |
| 2003/0077332 A1* | 4/2003 | Godfrey | A61K 33/30 424/642 |
| 2004/0042978 A1 | 3/2004 | Embro | |
| 2004/0122088 A1 | 6/2004 | Newsome et al. | |
| 2004/0198998 A1 | 10/2004 | Holerca et al. | |
| 2006/0024252 A1 | 2/2006 | Esposito et al. | |
| 2007/0071698 A1 | 3/2007 | Doss | |
| 2009/0220444 A1 | 9/2009 | Teckenbrock et al. | |
| 2010/0021573 A1 | 1/2010 | Gonzalez et al. | |
| 2010/0266480 A1 | 10/2010 | Huang | |
| 2010/0330163 A1 | 12/2010 | Soparkar | |
| 2011/0076309 A1 | 3/2011 | Misner et al. | |
| 2011/0229536 A1 | 9/2011 | Kvitnitsky et al. | |
| 2013/0017240 A1 | 1/2013 | Porter et al. | |
| 2014/0170086 A1 | 6/2014 | Pan et al. | |

FOREIGN PATENT DOCUMENTS

| | | | |
|---|---|---|---|
| CN | 103156073 | | 6/2013 |
| CN | 103535536 | | 1/2014 |
| DE | 735096 | | 5/1943 |
| EP | 0083486 | | 12/1982 |
| EP | 0108937 | | 5/1984 |
| EP | 0508524 | | 10/1992 |
| EP | 0514553 | | 11/1992 |
| EP | 0842664 | | 5/1998 |
| EP | 1021158 | | 7/2000 |
| EP | 1064946 | | 1/2001 |
| EP | 1203575 | | 5/2002 |
| EP | 1319394 | | 6/2003 |
| EP | 1935395 | | 6/2008 |
| EP | 1529775 | | 5/2011 |
| FR | 2241301 | | 3/1975 |
| GB | 2052978 | | 2/1981 |
| GB | 2109685 | | 6/1983 |
| GB | 2243775 | | 11/1991 |
| JP | S57-158724 | | 9/1982 |
| JP | 2004175790 | | 6/2004 |
| JP | 2009084201 | | 4/2009 |
| JP | 2010132639 | | 6/2010 |
| WO | WO86/00004 | | 1/1986 |
| WO | WO 91/02538 | * | 3/1991 |
| WO | WO9917735 | | 4/1999 |
| WO | WO0169087 | | 9/2001 |
| WO | WO2004054531 | | 7/2004 |
| WO | WO2004/064536 | | 8/2004 |
| WO | WO2007063507 | | 6/2007 |
| WO | WO2011053291 | | 5/2011 |
| WO | WO2011/088199 | | 7/2011 |
| WO | WO2011/123123 | | 10/2011 |
| WO | WO2014/098813 | | 6/2014 |
| WO | WO2014/098814 | | 6/2014 |
| WO | WO2014/098818 | | 6/2014 |
| WO | WO2014/098819 | | 6/2014 |
| WO | WO2014/098821 | | 6/2014 |
| WO | WO2014/098822 | | 6/2014 |
| WO | WO2014/098824 | | 6/2014 |
| WO | WO2014/099164 | | 6/2014 |
| WO | WO2014/099165 | | 6/2014 |
| WO | WO2014/099166 | | 6/2014 |
| WO | WO2014/099167 | | 6/2014 |
| WO | WO2014098825 | | 6/2014 |
| WO | WO2014098826 | | 6/2014 |
| WO | WO2014098828 | | 6/2014 |
| WO | WO2014098829 | | 6/2014 |
| WO | WO2014099039 | | 6/2014 |
| WO | WO2014099226 | | 6/2014 |
| WO | WO2014204439 | | 12/2014 |

OTHER PUBLICATIONS

International Search Report and Written Opinion for International Application No. PCT/US2012/070492 dated Oct. 22, 2013.
International Search Report and Written Opinion for International Application No. PCT/US2012/070498 dated Sep. 4, 2013.
International Search Report and Written Opinion for International Application No. PCT/US2012/070501 dated Oct. 21, 2013.
International Search Report and Written Opinion for International Application No. PCT/US2012/070505 dated Nov. 20, 2013.
International Search Report and Written Opinion for International Application No. PCT/US2012/070506 dated Oct. 14, 2013.
International Search Report and Written Opinion for International Application No. PCT/US2012/070513 dated Oct. 14, 2013.
International Search Report and Written Opinion for International Application No. PCT/US2012/070521 dated Sep. 30, 2013.
International Search Report and Written Opinion for International Application No. PCT/US2012/070525 dated Sep. 27, 2013.
International Search Report and Written Opinion for International Application No. PCT/US2012/070528 dated Sep. 30, 2013.
International Search Report and Written Opinion for International Application No. PCT/US2012/070534 dated Sep. 26, 2013.
International Search Report and Written Opinion for International Application No. PCT/US2012/070537 dated Oct. 11, 2013.
International Search Report and Written Opinion for International Application No. PCT/US2013/046268 dated Apr. 22, 2014.
International Search Report and Written Opinion for International Application No. PCT/US2013/050845 dated Aug. 13, 2014.
International Search Report and Written Opinion for International Application No. PCT/US2013/068852 dated Nov. 10, 2014.
International Search Report and Written Opinion for International Application No. PCT/US2013/068854 dated Oct. 20. 2014.
International Search Report and Written Opinion for International Application No. PCT/US2013/068859 dated Aug. 4, 2014.
International Search Report and Written Opinion for International Application No. PCT/US2013/068860 dated Oct. 22, 2014.
International Search Report and Written Opinion for International Application No. PCT/US2013/070932 dated Jul. 24, 2014.
International Search Report and Written Opinion for International Application No. PCT/US2014/042947 dated Aug. 22, 2014.
International Search Report and Written Opinion for International Application No. PCT/US2014/042948 dated Aug. 26, 2014.
International Search Report and Written Opinion for International Application No. PCT/US2014/043051 dated Feb. 18, 2015.
Kondrot, "The Importance of Zinc," http://www.healingtheeye.com/Articles/zinc.html, Feb. 21, 2012.
Liang et al., "In vitro scratch assay: a convenient and inexpensive method for analysis of cell migration in vitro," Nature Protocols, 2007, 2(2):329-333.
Lin et al., "The research on zinc coordination No. 5 odd structure in zinc complex with L-lysine," J. Molecular Science, 2000, 16(2):114-117, abstract only in English.
Lu et al., "Albumin as a zinc carrier: properties of its high-affinity zinc-binding site". Biochem. Soc. Trans., 2008, 36:1317-1321.
Lynch, "Zinc in the mouth, its interactions with dental enamel and possible effects on caries: a review of the literature," Int. Dent. J., Aug. 2011, Suppl 3:46-54.
Mavromichalis et al., "Growth-promoting efficacy of pharmacological doses of tetrabasic zinc chloride in diets for nursery pigs," Canadian Journal of Animal Science, pp. 387-391, Jan. 2001.
McAuliffe et al., "Metal complexes of sulphur-containing amino acids," Inorganica Chimica Acta Reviews, Dec. 1972, 6:103-121.
Moore et al., "Antibacterial activity of gutta-percha cones attributed to the zinc oxide component," Oral Surgery, 1982, 53:508-517.
Mosmann, "Rapid colorimetric assay for cellular growth and survival: Application to proliferation and cytotoxicity assays," J. Immunol. Methods, 1983, 65:55-63.

(56) References Cited

OTHER PUBLICATIONS

Pashley et al. Dentin permeability effects of desensitizing dentifrices in vitro. J Periodontol. 1984;55(9):522-525.

Prasad, "Zinc:role in immunity, oxidative stress and chronic inflammation,"Current Opinion in Clinical Nutrition and Metabolic Care, 2009, 12:646-652.

Rigano, I., Zinc Lauryl Ether Sulphate—A New Approach to Skin Care, SOFW Journal, Apr. 2004, 128:26-33.

Schmetzer et al., "Wulfingite, $\epsilon$-Zn(OH)2, and simonkolleite, Zn5(OH)8C12•H2O, two new minerals from Richelsdorf, Hesse, F.R.G.," N. Jb. Miner. Mh., Apr. 1985, pp. 145-154.

Seil et al., "Antibacterial effect of zinc oxide nanoparticles combined with ultrasound," Nanotechology,2012, 23:495101.

Soderling et al., "Betaine-containing toothpaste relieves subjective symptoms of dry mouth," Acta Odontol. Scand., Apr. 1998, 56(2):65-9.

Stewart et al., "Interdomain zinc site on human albumin," PNAS, 2003, 100(7):3701-3706.

Tian et al., "Using DGGE profiling to develop a novel culture medium suitable for oral microbial communities," Molecular Oral Microbiology, 2010, 25(5):357-367.

Twetman et al., 2003, "Caries-preventative effect of fluoride toothpaste a systematic review," Acta Odontol Scand., Dec. 2003, 61(6):347-55.

Wachi et al., "Antibacterial compsn. Zinc oxide—solubilized by amino acid, amino acid hydrochloride and/or amino acid alkali metal salt," Sep. 1982, vol. 1982(45).

Wallhausser et al., "Antimicrobial Preservatives in Europe: Experience with preservatives used in pharmaceuticals and cosmetics," Develop. Biol. Standard, 1974, 24:9-28.

Yao et al., "An investigation at zirconium(IV)-glycine(CP-2) hybrid complex in bovine serum albumin protein matrix under varying conditions," J. of Materials Chemistry, 2011, 21:19005-19012.

Yousef et al., "In vitro antibacterial activity and minimum inhibitory concentration at zinc oxide and nano-particle zinc oxide against pathogenic strains," J. of Health Sciences, 2012, 2(4):38-42.

Zhu et al., "Synthesis and Crystal Structure of [Zn+{H2N(CH2)4CH(NH2)COONa}2SO4-]•H20," Chinese Science Bulletin, Sep. 1990, 35(18):1521-1525.

\* cited by examiner

ANTIPERSPIRANT PRODUCTS WITH PROTEIN AND ANTIPERSPIRANT SALTS

BACKGROUND OF THE INVENTION

Antiperspirants based on aluminum or aluminum/zirconium salts are known. These materials function as antiperspirants by plugging pores thereby blocking sweat release. Antiperspirant compositions containing aluminum or aluminum-zirconium salts tend to exhibit polymerization of these salts over time, forming species with molecular weights ranging from about 500 to about 500,000 g/mol. In general, lower molecular weight species have greater antiperspirant effect than higher molecular weight species. Without being bound by theory, it is believed that the smaller molecules more readily and more effectively occlude sweat pores, thereby producing the desired antiperspirant effect. Maintaining a relatively low molecular weight and avoiding excessive polymerization enhances the antiperspirant effect and moreover lowers the amount of antiperspirant salt which necessary to control perspiration.

Underarm deodorants control odor by eliminating the bacteria that cause odor. Conventional aluminum or aluminum-zirconium antiperspirant salts tend to be acidic in aqueous solution, a property which makes them effective bacteriocides, thereby providing a deodorant benefit, but which can also cause skin irritation.

Bovine serum albumin (also known as BSA or "Fraction V") is a serum albumin protein derived from the blood of cattle. It helps maintain the osmotic pressure needed for proper distribution of body fluids between intravascular compartments and body tissues, buffers pH, and acts as a carrier protein for various compounds such as steroids, fatty acids, and thyroid hormones, It is inexpensive, readily available and does not have enzymatic properties, making it useful in many laboratory applications, e.g., to coat plastic materials and prevent adhesion of reactant proteins to the plastic, to stabilize certain enzymes, and to provide a reference standard for protein concentration. The protein has 583 amino acids and a molecular weight of about 66.5 kD. Albumins have been found to contain a high-affinity zinc binding site. See, e.g., J Lu, A. J Stewart, P. J Sadler, T. J. T Pinheiro and C. A Blindauer. "Albumin as a zinc carrier: properties of its high-affinity zinc-binding site". *Biochem. Soc. Trans.* (2008) 36, 1317-1321. A. J Stewart, C. A Blindauer, S Berezenko, D Sleep and P. J Sadler. "Interdomain zinc site on human albumin". *PNAS.* (2003) 100. No.7. 3701-3706. Albumins such as BSA are not known for use in antiperspirant or deodorant formulations.

There is a need for additional antiperspirant active agents that provide molecular weight complexes of a size capable of plugging pores to block sweat, that provide deodorant/antibacterial efficacy, and that are less irritating to the skin than the acidic salts in conventional antiperspirants.

BRIEF SUMMARY OF THE INVENTION

We have discovered that zinc antiperspirant salts are stable and soluble in concentrated formulations, but provide a precipitate upon use which blocks the pores, thereby providing an antiperspirant effect, and also kills bacteria which cause odors, thereby providing a deodorant benefit. Zinc antiperspirant salts may be for example a zinc X halide, wherein X is an amino acid or trimethylglycine, i.e., a complex of zinc ion, amino acid residue or trimethylglycine residue, and halide ion, such as zinc lysine chloride complexes. In one embodiment, the invention provides a composition comprising zinc X halide and/or zinc X halide precursor materials which form a zinc X halide in situ (for example zinc ion source plus an amino acid hydrohalide, or zinc halide plus an amino acid, or zinc ion source plus halogen acid plus amino acid). The zinc ion source to produce the zinc X halide is a material that can release $Zn^{++}$ in aqueous solution in the presence of an amino acid, for example zinc oxide or tetrabasic zinc chloride. Trimethylglycine as used throughout refers to N,N,N-trimethylglycine.

A particularly effective zinc antiperspirant salt is the zinc-lysine-HCl complex, sometimes referred to herein as ZLC, formed from a mixture of zinc oxide and lysine hydrochloride. The chemical structure of ZLC is $[Zn(C_6H_{14}N_2O_2)_2Cl]^+Cl^-$. This salt has key features (e.g., conductivity, hydrolysis reaction and protein flocculation) which make it competitive with commercial antiperspirant salts. Like conventional aluminum or aluminum-zirconium antiperspirant salts, zinc antiperspirant salts such as ZLC form precipitates under sweat conditions that can plug the pores and block sweat release. The mechanism is unusual. As the amount of water increases, rather than going into or remaining in solution as the solution becomes more dilute, as would typically be the case for an ionic complex, the ZLC complex hydrolyzes, to provide a relatively insoluble zinc oxide precipitate, thereby permitting further plugging of the pores and/or controlled deposition of zinc oxide on the skin. The zinc is moreover antibacterial, and so in addition to providing a precipitate which blocks sweat release from the pores, it provides a deodorant benefit by reducing odor-causing bacteria. Finally, the ZLC may be provided in a formulation which is approximately pH neutral, which is less irritating to the skin and less damaging to clothing than the currently-used aluminum or aluminum-zirconium antiperspirant salts, which are quite acidic in formulation, or current deodorant formulations, which typically contain high levels of alkali fatty acid salts and may be quite basic.

Zinc oxide is weakly soluble at low pH, however, and as sweat has a pH of 5-6, the sweat can reduce the levels of precipitation of the zinc oxide compared to precipitation levels at neutral pH. Moreover, the sweat can gradually dissolve the depositions, reducing the duration of action of the formulation. We have discovered that this problem can be ameliorated by co-formulating the product with a soluble protein, for example a protein having a high-affinity zinc binding domain, such as an albumin, e.g., bovine serum albumin. The protein and the zinc salt together form a precipitate upon use and dilution with sweat, which precipitate is resistant to acid. The formulation comprising the zinc antiperspirant salt together with the protein thus has enhanced efficacy as an antiperspirant.

The protein can also be used to enhance the efficacy of other antiperspirant salts comprising a polyvalent cation, for example antiperspirant complexes of (i) aluminum and optionally zirconium, (ii) chlorohydrate, and (iii) optionally an amino acid and/or ammonium acid, for example glycine and/or trimethylglycine, e.g., aluminum zirconium tetrachlorohydrex glycine.

The invention thus provides antiperspirant products comprising a protein, e.g., BSA, and an antiperspirant salt, e.g., a zinc antiperspirant salt, e.g., ZLC, as well as methods of making and using such products. The invention further provides methods of reducing sweat comprising applying the composition to skin, and methods of killing bacteria comprising contacting the bacteria with the composition.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

The invention therefore provides, in a first embodiment, an antiperspirant formulation ("Formulation 1") comprising a protein and an antiperspirant salt in combination with a cosmetically acceptable carrier, e.g., 1.1. Formulation 1 wherein the antiperspirant salt is selected from aluminum chlorohydrates, aluminum-zirconium chlorohydrates, and zinc chlorides; and amino acid or glycol complexes thereof.

1.2. Formulation 1.1, wherein the antiperspirant salt is a zinc X halide complex, wherein X is an amino acid or trimethylglycine.

1.3. Any of Formulation 1.1 to 1.2, wherein the zinc X halide is formed from precursors, wherein the precursors are a zinc ion source, an X source, and a halide source, wherein the halide source can be part of the zinc ion source, the X source, or a halogen acid.

1.4. Any of Formulation 1.1 to 1.3, wherein the zinc ion source is at least one of zinc oxide, zinc chloride, tetrabasic zinc chloride, zinc carbonate, zinc nitrate, zinc citrate, and zinc phosphate.

1.5. Any of Formulation 1.1 to 1.4, wherein the X source is at least one of a basic amino acid, lysine, arginine, glycine, and trimethylglycine.

1.6. Any of Formulation 1.1 to 1.5, wherein the zinc X halide is made by combining zinc oxide with an amino acid hydrohalide.

1.7. Any of Formulation 1.1 to 1.6, wherein the zinc X halide is made by combining TBZC with an amino acid hydrohalide, an amino acid, or trimethylglycine, optionally the zinc X halide is made by combining TBZC with lysine, lysine hydrochloride, or trimethylglycine.

1.8. Any of Formulation 1.1 to 1.7, wherein the zinc X halide has the formula $ZnX_2Hal_2$ or $ZnX_3Hal_2$, wherein Zn is a divalent zinc ion and Hal is a halide ion.

1.9. Any of Formulation 1.1 to 1.8, wherein a total amount of zinc present in the composition is 0.05 to 10% by weight.

1.10. Any of Formulation 1.1 to 1.9, wherein the zinc X halide is present in an amount of 0.05 to 40% by weight of the composition, optionally at least 0.1, at least 0.2, at least 0.3, at least 0.4, at least 0.5, at least 1, at least 2, at least 3, or at least 4 up to 40% by weight of the composition, or, optionally, 0.1 up to 30%, up to 20%, up to 10%, up to 5%, up to 4%, up to 3%, up to 2%, or up to 1% by weight of the composition.

1.11. Any of Formulation 1.1 to 1.10, wherein a molar ratio of zinc to X in the zinc X halide is 2:1 to 1:4, optionally 1:1 to 1:4, 1:2 to 1:4, 1:3 to 1:4, 2:1 to 1:3, 2:1 to 1:2, 2:1 to 1:1, or 1:3.

1.12. Any of Formulation 1.1 to 1.11, wherein the halide is chloride.

1.13. Any of Formulation 1.1 to 1.12, wherein the zinc X halide is zinc lysine chloride.

1.14. Any of Formulation 1.1 to 1.13, wherein the zinc X halide is $ZnLysine_2Cl_2$ or $ZnLysine_3Cl_2$.

1.15. Any of Formulation 1.1 to 1.14, wherein the antiperspirant salt is a zinc-lysine-chloride complex, having the formula $[Zn(C_6H_{14}N_2O_2)_2Cl]^+Cl^-$, optionally in hydrate form.

1.16. Any of the foregoing formulations wherein the protein is a soluble protein comprising a high affinity zinc binding site, e.g., a serum albumin, e.g., bovine serum albumin.

1.17. Any of the foregoing formulations wherein the antiperspirant salt is a zinc-lysine-chloride complex in crystalline form, e.g. in hydrate form, e.g. a monohydrate or dihydrate, e.g., having a structure wherein the Zn cation is coordinated by two lysine ligands with two nitrogen atoms from alpha $NH_2$ groups of the two lysine ligands and two oxygen atoms from carboxylic groups of the two lysine ligands in an equatorial plane, having a distorted square-pyramidal geometry with the apical position occupied by a chlorine atom, to form a positive cation moiety, with which a chloride anion is combined to form an ionic salt.

1.18. Any of the foregoing formulations wherein the antiperspirant salt is a zinc antiperspirant salt which forms a zinc oxide precipitate upon increasing dilution with water.

1.19. Any of the foregoing formulations wherein the antiperspirant salt is present in the amount of 5-35% of the formulation by weight, e.g. 10-25%.

1.20. Any of the foregoing formulations wherein the antiperspirant salt is a zinc antiperspirant salt present in the amount of 5%-35% by weight of the formulation, e.g., 10-25%.

1.21. Any of the foregoing formulations wherein the antiperspirant salt is a zinc antiperspirant salt and wherein the total amount of zinc present in the composition is 0.2 to 10% by weight of the formulation, e.g. 2-3%.

1.22. Any of the foregoing formulations wherein the amount of protein in the composition is 0.01-5%, e.g., 0.05-1%, by weight of the composition.

1.23. Any of the foregoing formulations wherein the pH of the formulation is 6-8, e.g., 6.5-7.5, e.g., approximately neutral.

1.24. Any of the foregoing formulations, wherein the cosmetically acceptable carrier comprises less than 10% water, e.g., less than 5% water, e.g., is substantially anhydrous.

1.25. Any of the foregoing formulations wherein the composition comprises not more than 85% water.

1.26. Any of the foregoing formulations wherein the cosmetically acceptable carrier comprises one or more ingredients selected from water-soluble alcohols (such as $C_{2-8}$ alcohols including ethanol); glycols (including propylene glycol, dipropylene glycol, tripropylene glycol and mixtures thereof); glycerides (including mono-, di- and triglycerides); medium to long chain organic acids, alcohols and esters; surfactants (including emulsifying and dispersing agents); additional amino acids; structurants (including thickeners and gelling agents, for example polymers, silicates and silicon dioxide); emollients; fragrances; and colorants (including dyes and pigments).

1.27. Any of the foregoing formulations, wherein the composition is in the form of an antiperspirant stick, an aerosol antiperspirant spray, or a liquid roll-on antiperspirant.

The invention further provides methods of reducing perspiration comprising applying an antiperspirant effective amount of any of Formulation 1, et seq. to the skin, methods of reducing body odor comprising applying a deodorant-effective amount of any of Formulation 1, et seq. to the skin, and methods of killing bacteria comprising contacting the bacteria with contacting with any of Formulation 1, et seq.

The invention further provides a method of making any of Formulation 1, et seq. comprising forming the antiperspirant salt in aqueous solution (e.g., wherein the antiperspirant salt is a zinc-lysine-chloride complex, by a combining zinc oxide and lysine hydrochloride in aqueous solution), optionally isolating the salt in solid form, and admixing with a protein and a cosmetically acceptable carrier.

The invention further provides (i) the use of any of Formulation 1, et seq. to kill bacteria, reduce perspiration, and/or reduce body odor; and (iii) any of Formulation 1, et seq. for use in killing bacteria, reducing perspiration, and/or reducing body odor.

The invention further provides the use of a protein, e.g., use of a serum albumin, e.g., use bovine serum albumin, in the manufacture of an antiperspirant formulation, e.g., an antiperspirant formulation according to any of Formulation 1, et seq.

It will be understood that, although the antiperspirant salt may be primarily in the form of a complex, there may be some degree of equilibrium with the salt precursor materials, so that the proportion of material which is actually in complex compared to the proportion in precursor form may vary depending on the precise conditions of formulation, concentration of materials, pH, presence or absence of water, presence or absence of other charged molecules, and so forth. For example, wherein the antiperspirant salt is a zinc-lysine-chloride complex, e.g., ZLC, the formulation may comprise an equilibrium fraction of zinc oxide and lysine hydrochloride precursor materials.

The antiperspirant salt and the protein of Formulation 1, et seq., can be incorporated into a suitable, cosmetically acceptable base, for example a stick, roll-on, spray or aerosol, for application to the underarm. Following application, in the presence of charged molecules such as proteins found on the skin, the salt will will flocculate, forming plugs which block sweat release. Additional water from sweat can moreover dilute the formulation, causing the complex to decompose, e.g., in the case of a zinc-lysine-chloride complex resulting in precipitation of zinc oxide, which can reduce sweat and odor as described above.

As used herein, the term antiperspirant can refer to any material that can form a plug in a pore to reduce sweating, or antiperspirant refers to those materials classified as antiperspirants by the Food and Drug Administration under 21 CFR part 350. Antiperspirants may also be deodorants, particularly in the case of this invention, as zinc has antibacterial properties and can reduce odor-causing bacteria on the skin.

In some embodiments, the antiperspirant salt for use in Formulation 1, et seq. is an aluminum antiperspirant salt or aluminum-zirconium antiperspirant salt, e.g., as described in 21 CFR 350.10, e.g., salts which meet the aluminum to chloride, aluminum to zirconium, and aluminum plus zirconium to chloride atomic ratios described in the U.S. Pharmacopeia-National Formulary. Exemplary aluminum chlorohydrates, aluminum-zirconium chlorohydrates and complexes thereof include:

(a) Aluminum chloride up to 15 percent, calculated on the hexahydrate form, in an aqueous solution nonaerosol dosage form.
(b) Aluminum chlorohydrate up to 25 percent.
(c) Aluminum chlorohydrex polyethylene glycol up to 25 percent.
(d) Aluminum chlorohydrex propylene glycol up to 25 percent.
(e) Aluminum dichlorohydrate up to 25 percent.
(f) Aluminum dichlorohydrex polyethylene glycol up to 25 percent.
(g) Aluminum dichlorohydrex propylene glycol up to 25 percent.
(h) Aluminum sesquichlorohydrate up to 25 percent.
(i) Aluminum sesquichlorohydrex polyethylene glycol up to 25 percent.
(j) Aluminum sesquichlorohydrex propylene glycol up to 25 percent.
(k) Aluminum zirconium octachlorohydrate up to 20 percent.
(l) Aluminum zirconium octachlorohydrex gly up to 20 percent.
(m) Aluminum zirconium pentachlorohydrate up to 20 percent.
(n) Aluminum zirconium pentachlorohydrex gly up to 20 percent.
(o) Aluminum zirconium tetrachlorohydrate up to 20 percent.
(p) Aluminum zirconium tetrachlorohydrex gly up to 20 percent.
(q) Aluminum zirconium trichlorohydrate up to 20 percent.
(r) Aluminum zirconium trichlorohydrex gly up to 20 percent.

The concentration of ingredients in (b) through (j) above is calculated on an anhydrous basis, omitting from the calculation any buffer component present in the compound, in an aerosol or nonaerosol dosage form. The concentration of ingredients in paragraphs (k) through (r) above is calculated on an anhydrous basis, omitting from the calculation any buffer component present in the compound, in a nonaerosol dosage form.

The composition can comprise zinc antiperspirant salts, for example zinc-amino acid-halide complexes, e.g. zinc-lysine-chloride for example ZLC, and/or precursors thereof, for example zinc oxide and lysine hydrochloride in the case of a zinc-lysine-chloride complex. In one embodiment, the salt is prepared at room temperature by mixing the precursors in an aqueous solution. The in situ formation provides ease of formulation. The precursors can be used instead of first having to form the salt. In another embodiment, the water permitting formation of the salt from the precursor comes from sweat that comes into contact with the composition after application.

In some embodiments, the antiperspirant salt is a zinc antiperspirant salt, providing the total amount of zinc in the composition is 0.05 to 8% by weight of the composition. In other embodiments, the total amount of zinc is at least 0.1, at least 0.2, at least 0.3, at least 0.4, at least 0.5, or at least 1 up to 8% by weight of the composition. In other embodiments, the total amount of zinc in the composition is less than 5, less than 4, less than 3, less than 2, or less than 1 to 0.05% by weight of the composition. For example, the zinc content may be 2-3%.

In certain embodiments, the composition is anhydrous. By anhydrous, there is less than 5% by weight water, optionally less than 4, less than 3, less than 2, less than 1, less than 0.5, less than 0.1 down to 0% by weight water.

When provided in an anhydrous composition, precursors, e.g., zinc oxide and lysine hydrochloride, will not significantly react. When contacted with a sufficient amount of water, which can be in the form of sweat, the precursors will then react to form the desired salt, e.g., ZLC, which when introduced into a sweat duct will flocculate with protein and/or hydrolyze with water and/or sweat to form a precipitate to block the sweat duct.

In certain embodiments, the antiperspirant salt can have a conductivity of greater than 8000, optionally greater than 9000, greater than 10,000, or greater than 12,000 µS/cm The cosmetically acceptable carrier represents all other materials in the composition other than the antiperspirant salt (including precursors) and the protein. The amount of carrier is then the amount to reach 100% by adding to the weight of antiperspirant salt (including precursors) and the protein.

For antiperspirant/deodorant compositions, the carrier can be any carrier that is used for antiperspirants/deodorants. The carrier can be in the form of a stick, a gel, a roll-on, or an aerosol. For stick formulations, the carrier may include oils and/or silicones and gelling agents. An example of a formulation can be found in US2011/0076309A1, incorporated by reference herein.

Optional ingredients that can be included in an antiperspirant and/or deodorant formulation of the compositions of the invention include solvents; water-soluble alcohols such as $C_{2-8}$ alcohols including ethanol; glycols including propylene glycol, dipropylene glycol, tripropylene glycol and mixtures thereof; glycerides including mono-, di- and triglycerides; medium to long chain organic acids, alcohols and esters; surfactants including emulsifying and dispersing agents; amino acids including glycine; structurants including thickeners and gelling agents, for example polymers, silicates and silicon dioxide; emollients; fragrances; and colorants including dyes and pigments. If desired, an antiperspirant and/or deodorant agent additional to the ZLC, e.g., any of Complex 1, et seq. can be included, for example an odor reducing agent such as a sulfur precipitating agent, e.g., copper gluconate, zinc gluconate, zinc citrate, etc.

The antiperspirant compositions can be formulated into topical antiperspirant and/or deodorant formulations suitable for application to skin, illustratively a stick, a gel, a cream, a roll-on, a soft solid, a powder, a liquid, an emulsion, a suspension, a dispersion or a spray. The composition can comprise a single phase or can be a multi-phase system, for example a system comprising a polar phase and an oil phase, optionally in the form of a stable emulsion. The composition can be liquid, semi-solid or solid. The antiperspirant and/or deodorant formulation can be provided in any suitable container such as an aerosol can, tube or container with a porous cap, roll-on container, bottle, container with an open end, etc.

The compositions can be used in a method to reduce sweating by applying the composition to skin. In certain embodiments, the application is to axilla. Also, the compositions can be used to kill bacteria by contacting bacteria with the composition. For example, in one embodiment, the combination of the amino acid or amino acid hydrohalide with the zinc oxide increases the availability of zinc ions, which can then kill bacteria and reduce sweat.

Thus the invention provides (i) a method for controlling perspiration comprising applying to skin an antiperspirant effective amount of a formulation of any embodiment embraced or specifically described herein, e.g., any of Formulation 1 et seq.; and (ii) a method for controlling odor from perspiration comprises applying to skin a deodorant effective amount of a formulation of any embodiment embraced or specifically described herein, e.g., any of Formulation 1 et seq.

Unless stated otherwise, all percentages of composition components given in this specification are by weight based on a total composition or formulation weight of 100%.

Unless otherwise specifically identified, the ingredients for use in the compositions and formulations of the present invention are preferably cosmetically acceptable ingredients. By "cosmetically acceptable" is meant suitable for use in a formulation for topical application to human skin. A cosmetically acceptable excipient, for example, is an excipient which is suitable for external application in the amounts and concentrations contemplated in the formulations of this invention, and includes for example excipients which are "Generally Recognized as Safe" (GRAS) by the United States Food and Drug Administration.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

EXAMPLE 1

Synthesis and Characterization of Zinc-Lysine Complex ZLC

The general reaction for formation of ZLC is as follows:

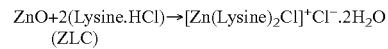

$$ZnO+2(Lysine.HCl)\rightarrow[Zn(Lysine)_2Cl]^+Cl^-.2H_2O$$
(ZLC)

A 2:1 molar ratio of ZnO:Lysine.HCl suspension is prepared with stirring at room temperature for about 12 hours. The mixture is centrifuged. 1 ml of supernatant is transferred into an NMR tube. The NMR tube is then placed in a closed test tube filled with ethanol for crystal growth. A number of colorless, cubic crystals are formed after a week. The crystal structure of ZLC crystal is determined by single crystal X-ray diffraction. ZLC has an empirical formula as $C_{12}H_{32}N_4O_6Cl_2Zn$ with molecular weight of 463 g/mol. It displays a distorted square-pyramidal geometry with the apical position occupied by a Cl atom. This novel structure gives rise to a positive cation moiety, to which a Cl anion is combined to form an ionic salt.

Laboratory scale-up synthesis of pure ZLC powder: 2 mole of LysineHCl is dissolved in 1000 ml DI water with stirring at room temperature, 1 mole of solid ZnO is added slowly to the LysineHCl solution with stirring and the stirring is continued at RT overnight (about 12 hours). The suspension solution is centrifuged at high speed for 15 mins. The supernatant is slowly poured into EtOH. A precipitate is formed immediately. Approximately 5-8 ml EtOH is needed to get 1 g powder. The EtOH solvent with powder is filtered, and an off-white powder is obtained. The powder is placed in a 50° C. oven for drying and an 88% yield of product is obtained.

EXAMPLE 2

Mechanisms of Sweat Reduction

Hydrolysis reaction: A 185 mg/ml ZLC solution is prepared and diluted several-fold and aged in a 37° C. oven over 5 hours for turbidity studies. A white precipitate forms as the solution is diluted. Turbidity of the solutions is measured using a nephelometer, results being given in nephelometric turbidity units (NTU). Table 1 shows a comparison of pH and turbidity before and after aging, showing an increase in turbidity with dilution and with aging:

TABLE 1

|  | 185 mg/ml | 92.5 mg/ml | 46.25 mg/ml | 23.125 mg/ml | 11.56 mg/ml | 5.78 mg/ml |
|---|---|---|---|---|---|---|
| initial pH | 6.8 | 7 | 7.4 | 7.7 | 7.8 | 8 |
| initial turbidity (NTU) | 4.7 | 2.8 | 1.5 | 0.7 | 14.8 | 40.1 |
| pH after aging | 6.8 | 7 | 7.4 | 7.7 | 7.8 | 8 |
| turbidity after aging (NTU) | 4.1 | 2.6 | 2.8 | 247.4 | >1000 | >1000 |

The precipitates formed in the 8×, 16× and 32× diluted solutions are collected by centrifugation and identified as crystalline ZnO by PXRD. From the supernatant, a single crystal is grown and shown by X-ray diffraction to be Lysine Monohydrochloride Dihydrate (Lysine.HCl.2H$_2$O). These data indicate that the ZLC complex disassociates upon dilution, with consequent precipitation of zinc oxide.

The mechanism of the ZLC hydrolysis reaction can be expressed as

[Zn(Lysine)$_2$Cl]$^+$Cl$^-$.2H$_2$O+H$_2$O→ZnO+ Lysine.HCl.2H$_2$O

In an underarm product, a mixture of ZnO+lysine HCl, in the presence of sweat, will form ZLC, which will enter the sweat duct and form a plug of ZnO.

Flocculation: Another mechanism by which the ZLC blocks sweat release involves flocculation of ZLC in the presence of protein. Bovine Serum Albumin (BSA) is used as the protein in this study. Control solution (DI water) and three 1% BSA aqueous solutions with different pH are prepared as set forth on Table 2.

TABLE 2

|  | sample 1 | sample 2 | sample 3 |
|---|---|---|---|
| H$_2$O | 15 ml | 15 ml | 15 ml |
| BSA | 0 g | 155.1 mg | 155.2 mg |
| % BSA w/w | 0% | 1% | 1% |
| pH | 6.4 | 7.2 | adjusted to 5.1 |
| Turbidity (NTU) | 0.35 | 3.6 | 10.6 |
| Observation | Transparent | Transparent | Transparent |

ZLC powder is added to the above samples to study the interaction between ZLC and BSA and to determine whether ZLC has astringent properties, i.e., whether it can form a precipitate and thus behave as an antiperspirant. Turbidity and pH of solutions are measured 5 hours after the mixtures were placed in a 37° C. oven, and the results are shown in Table 3.

TABLE 3

|  | sample 1 | sample 2 | sample 3 |
|---|---|---|---|
| ZLC added | 151.1 mg | 151.1 mg | 150.9 mg |
| ZLC concentration in solution | about 0.98% w/w or 15 mg/ml | about 0.96% w/w or 15 mg/ml | about 0.96% w/w or 15 mg/ml |
| observation | transparent solution becomes slightly cloudy | a lot white precipitate formed, solution becomes very cloudy | a lot white precipitate formed, solution becomes very cloudy |
| pH | 8 | 8.2 | 8 |
| Turbidity (NTU) | 357 | >1000 | >1000 |

Thus, in the sweat duct (pH=5-7), ZLC will hydrolyze to insoluble ZnO to physically block the sweat ducts. In addition, ZLC also has the ability to flocculate proteins, such as BSA, in the sweat, thus enhancing the formation of "plugs" in the sweat ducts.

EXAMPLE 3

Antibacterial Effects

A zone of inhibition test is conducted on several materials: zinc oxide, lysine hydrochloride, and ZLC. The method involves making a lawn of freshly prepared bacterial culture on TSA (trypticase soy agar) plates. Sterile filter paper discs are seeded with 20 µl of test sample (supernatant or mixture). Sample-coated filter paper discs are air dried and applied onto the bacterial lawn on TSA plates. Plates are incubated for 20 hours at 37° C. ZLC has better antibacterial activity than zinc oxide alone or lysine hydrochloride alone.

EXAMPLE 4

Formulation Combining ZLC and BSA

The Zn-Lysine.HCl salt (ZLC) is believed to be useful as a non-aluminum antiperspirant active due to its formation of insoluble ZnO by dilution of water. The insoluble ZnO re-formed in sweat ducts is able to prevent sweat from coming out skin. Although ZnO is insoluble in water, it is gradually soluble in a weak acidic environment, which will reduce efficacy as it forms plugs at the sweat ducts (i.e. in sweat where the pH varies from 5 to 6). We previously found that a combination of current AP active salts (Al and Zr salts) and BSA protein has optimal precipitation at pH around 5.5 (in the pH range of human sweat) due to charge neutralization mechanism, and the novel positively charged ZLC salt could also form precipitation with negatively charged BSA protein at acid sweat pH through the same mechanism. We also considered that the high-affinity zinc-binding site on serum albumin could provide an additional stabilizing influence.

In the following study, four ZLC-BSA mixture solutions are prepared with 2.53% Zn and varied BSA concentrations (0.05%, 0.1%, 0.5% and 1% by weight) in deionized water. The detailed CP4 and BAS concentration are listed in Table 4.

TABLE 4

|  | ZLC solution (2.53% Zn) | BSA | Final pH | observation |
|---|---|---|---|---|
| ZLC-BSA 0.05% | 122.7 g | 61.8 mg | 7 | All solutions |
| ZLC-BSA 0.1% | 122.8 g | 122.9 mg | 7 | are |

TABLE 4-continued

| | ZLC solution (2.53% Zn) | BSA | Final pH | observation |
|---|---|---|---|---|
| ZLC-BSA 0.5% | 124.7 g | 623.3 mg | 7 | transparent in the final pH |
| ZLC-BSA 1% | 117.4 g | 1174.4 mg | 7 | |

The pH of the solutions is adjusted to 3, 4, 5, 6, 7, 8, 9, 10 and 11 to observe the formation of precipitation. Precipitate is formed in all solutions at pH ranging from 3 to 5. Slight precipitation is found at pH 6 in the solution containing high concentration of BSA (0.5% and 1%). All solutions appear clear at pH 8. A small amount of precipitation is also found at pH 9 and 10. At pH 11, precipitate is formed in all solutions. As the concentration of BSA increases, there is an increased amount of precipitation formed at low pH range from 3 to 5. In addition, the pH of pure ZLC solution and the pH of pure 0.5% BSA solution are adjusted to the same range to observe the formation of precipitation. No precipitation is found in pure ZLC solution and or in pure 0.5% BSA aqueous solution at pH 3-11. The formation of precipitation in acid pH requires both ZLC and BSA to be present in solution.

As shown in Example 4, precipitates form when ZLC solution is diluted. The ZLC-BSA solution also forms precipitate when it is further diluted. The following experiment shows varying dilutions to study the formation of precipitation of ZLC-BSA solution at same 0.5% BSA level. ZLC-BSA solution with 0.5%BSA is diluted into 2 fold, 4 fold, 8 fold, 16 fold and 32 fold. The pHs of dilutions are 7.33, 7.45, 7.79, 8.08 and 8.16, respectively. The 16 fold and 32 fold dilutions appear cloudy instantly after preparation.

Whereas BSA incorporated into a conventional aluminum or aluminum-zirconium antiperspirant salt formulation would tend to form precipitates in formulation due to the typically low pH of these formulations, BSA can be formulated with ZLC in an approximately neutral formulation, and then provide an acid resistant ZLC-BSA complex upon use, with increasing dilution from sweat, thus enhancing the efficacy of the antiperspirant.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The invention claimed is:

1. An antiperspirant formulation comprising bovine serum albumin and an antiperspirant salt in combination with a cosmetically acceptable carrier, wherein the antiperspirant salt is a zinc lysine chloride complex.

2. The antiperspirant formulation according to claim 1, wherein the zinc lysine chloride complex is formed from precursors, wherein the precursors are a zinc ion source, a lysine source, and a chloride source, wherein the chloride source can be part of the zinc ion source, the lysine source, or a chlorine acid.

3. The antiperspirant formulation according to claim 2, wherein the zinc ion source is selected from the group consisting of zinc oxide, zinc chloride, tetrabasic zinc chloride, zinc carbonate, zinc nitrate, zinc citrate, and zinc phosphate.

4. The antiperspirant formulation according to claim 1, wherein the zinc lysine chloride complex is made by combining zinc oxide with lysine hydrochloride.

5. The antiperspirant formulation according to claim 1, wherein the zinc lysine chloride complex is made by combining tetrabasic zinc chloride with lysine, or lysine hydrochloride.

6. The antiperspirant formulation according to claim 1, wherein a total amount of zinc present in the composition is 0.05 to 10% by weight.

7. The antiperspirant formulation according to claim 1, wherein the zinc lysine chloride complex is present in an amount of 0.05 to 40% by weight of the composition.

8. The antiperspirant formulation according to claim 1, wherein a molar ratio of zinc to lysine in the zinc lysine chloride complex is 2:1 to 1:4, or 1:1 to 1:4, or 1:2 to 1:4, or 1:3 to 1:4, or 2:1 to 1:3, or 2:1 to 1:2, or 2:1 to 1:1, or 1:3.

9. The antiperspirant formulation according to claim 1, wherein the zinc lysine chloride complex is $ZnLysine_2Cl_2$ or $ZnLysine_3Cl_2$.

10. The antiperspirant formulation of claim 1, wherein the zinc-lysine-chloride complex has the formula $[Zn(C_6H_{14}N_2O_2)_2Cl]^+Cl^-$, or has the formula $[Zn(C_6H_{14}N_2O_2)_2Cl]^+Cl^-$ in a hydrate form.

11. The antiperspirant formulation of claim 1 wherein the amount of protein in the composition is 0.01-5% by weight of the composition.

12. The antiperspirant formulation of claim 1 wherein the pH of the formulation is 6-8.

13. The antiperspirant formulation of claim 1 wherein the cosmetically acceptable carrier comprises one or more ingredients selected from the group consisting of water-soluble alcohols; glycols; glycerides; medium to long chain organic acids, alcohols and esters; surfactants; additional amino acids; structurants; emollients; fragrances; and colorants.

14. The antiperspirant formulation of claim 1 wherein the composition is in the form of an antiperspirant stick, an aerosol antiperspirant spray, or a liquid roll-on antiperspirant.

15. A method of reducing perspiration, reducing body odor and/or killing bacteria, comprising applying an effective amount of the antiperspirant formulation of claim 1 to skin.

* * * * *